(12) United States Patent
Eliaz

(10) Patent No.: US 8,426,567 B2
(45) Date of Patent: Apr. 23, 2013

(54) METHOD FOR ENHANCING MAMMALIAN IMMUNOLOGICAL FUNCTION

(75) Inventor: Isaac Eliaz, Sebastopol, CA (US)

(73) Assignee: Econugenics, Inc., Santa Rosa, CA (US)

( * ) Notice: Subject to any disclaimer, the term of this patent is extended or adjusted under 35 U.S.C. 154(b) by 1045 days.

(21) Appl. No.: 11/485,955

(22) Filed: Jul. 14, 2006

(65) Prior Publication Data

US 2007/0049551 A1    Mar. 1, 2007

Related U.S. Application Data

(60) Provisional application No. 60/711,415, filed on Aug. 26, 2005.

(51) Int. Cl.
 *C08B 37/06* (2006.01)
 *C08B 37/04* (2006.01)
 *C07H 1/00* (2006.01)
 *A61K 31/732* (2006.01)
 *A61K 31/734* (2006.01)

(52) U.S. Cl.
 USPC ............ 536/2; 536/3; 536/124; 514/54

(58) Field of Classification Search ........... 536/2, 3, 536/124; 514/54
 See application file for complete search history.

(56) References Cited

U.S. PATENT DOCUMENTS

| | | | | |
|---|---|---|---|---|
| 5,681,562 A | * | 10/1997 | Sobol et al. | 424/93.21 |
| 5,738,855 A | * | 4/1998 | Szu et al. | 424/258.1 |
| 6,274,566 B1 | | 8/2001 | Eliaz et al. | |
| 6,462,029 B1 | | 10/2002 | Eliaz | |
| 7,078,434 B1 | * | 7/2006 | Drieu et al. | 514/468 |
| 2005/0026849 A1 | * | 2/2005 | Singh et al. | 514/26 |

FOREIGN PATENT DOCUMENTS

| | | | |
|---|---|---|---|
| JP | 11236334 A | * | 8/1999 |
| WO | WO 9951276 A1 | * | 10/1999 |

OTHER PUBLICATIONS

Sweet et al (Toxicology and Immunotoxicology of Mercury: A Comparative Review in Fish and Humans, Journal of Toxicology and Environmental Health, Part B: Critical Reviews, vol. 4, Issue 2, pp. 161-205).*
Sweet et al (Toxicology and Immunotoxicology of Mercury: A Comparative Review in Fish and Humans, Journal of Toxicology and Environmental Health, Part B: Critical Reviews, 2001, vol. 4, Issue 2, pp. 161-205).*
Turner, "90 years on: A therapy to stimulate the phagocytes?" *Scand J. Immuno.* 48: 124-26 (1988).
Kakkanaiah et al., "Association of low concentrations of serum mannose-binding protein with recurrent infections in adults." *Clin. Diag. Lab. Immunol.* 5: 319-21 (1998).
Pienta et al., "Inhibition of spontaneous metastasis in a rate prostate cancer model by oral administration of modified citrus pectin.", J. *Nat'l Cancer Inst.* 87: 348-52 (1995).
Dr. Eliaz.com, "Experience guidance for health and longevity: Health conditions," *at* http:/dreliaz.com/resources_inside. php?rid=1&fid= 1&fidkid=76.

* cited by examiner

*Primary Examiner* — Wu-Cheng Winston Shen
*Assistant Examiner* — Everett White
(74) *Attorney, Agent, or Firm* — Steven B. Kelber

(57) ABSTRACT

Low molecular weight modified pectin, particularly modified citrus pectin (MCP), and/or low molecular weight modified alginate is useful in a composition for stimulating the immune response of a mammal, particularly a human. Modified pectin and/or modified alginate is administered in a composition in an amount sufficient to modulate, support, enhance or extend an immune response, particularly to an individual having an inadequate or reduced immune function. Stimulation of an immune response is evidenced by stimulation of cell-mediated immune function, humoral immune function, phagocytic function of mononuclear macrophages, and NK cell activity. The composition also may comprise well known pharmacologically acceptable agents, such as sulfured amino acids, cilantro, garlic, minerals, and herbs.

28 Claims, No Drawings

METHOD FOR ENHANCING MAMMALIAN IMMUNOLOGICAL FUNCTION

CROSS REFERENCE TO RELATED APPLICATIONS

This application claims the benefit of priority to Provisional U.S. Application Ser. No. 60/711,415, filed Aug. 26, 2005, which is incorporated by reference herein in its entirety.

BACKGROUND OF THE INVENTION

1. Technical Field

This invention pertains generally to methods of enhancing a mammalian immune response by administering a modified low molecular weight pectin composition.

2. Background of the Technology

Chemically or enzymatically modified pectins and similar alginates having an average molecular weight of 40,000 daltons or less effectively bind a variety of harmful circulating agents. Modified low molecular weight pectins, for example, exhibit a number of useful therapeutic properties based on their ability to bind a variety of compounds, including cholesterol, tumor emboli, heavy metals, toxins and calcium. U.S. Pat. Nos. 6,274,566 and 6,462,029, herein incorporated by reference in their entirety, disclose the use of low molecular weight modified alginates and low molecular weight modified pectins for the treatment of a variety of human conditions.

U.S. Pat. No. 6,274,566 specifically describes the use of modified alginates to treat diseases characterized by inadequate immune response, noting that the administration of mannose, a breakdown product of alginates, effectively stimulates the immune system. See also Turner, *Scand. J. Immunol.* 48: 124-26 (1988); Kakkanaiah et al., *Clin. Diag. Lab Immunol.* 5: 319-21 (1998). There is ongoing need, however, to identify additional compounds that are useful as immunostimulators.

SUMMARY OF THE INVENTION

The administration of low molecular weight modified pectin and/or low molecular weight modified alginate effectively stimulates the immune response of mammals. In one aspect of the invention, a method of administering a composition comprising a low molecular weight pectin and/or low a molecular weight modified alginate is used to modulate, support, enhance, or extend the immune response of a mammal (e.g., a human) having an inadequate or reduced immune function. Stimulation of a mammalian immune response may comprise stimulating cell-mediated immunity, humoral immunity, phagocytic mononuclear macrophage function, or NK cell activity. Modified pectins useful for the present invention include pectin oligosaccharide ("POS") and modified citrus pectin ("MCP"), such as that from Econugenics, Inc., distributed by Hangzhou Centrax Trading, Inc. as Centrax PectaSol MCP Powder.

The composition of the present invention may be administered orally or intravenously, or by any other manner effective to provide modified pectin and/or modified alginate in an amount sufficient to stimulate the immune response of a mammal. The present specification provides recommended dosing regimen. Modified pectin and/or modified alginate in the present composition may be combined with well known pharmacologically acceptable agents.

DETAILED DESCRIPTION OF THE INVENTION

The present invention provides methods for using low molecular weight modified pectin, including MCP and POS, and/or low molecular weight modified alginate to stimulate the immune response of a mammal. A stimulation of an immune response in a mammal that is administered the present composition includes any effect that modulates, supports, enhances, or extends the immune response. Such effects include, but are not limited to, stimulation of cell-mediated immunity, humoral immunity, phagocytic mononuclear macrophage function, or NK cell activity. While the present invention is not limited by a particular theory of a mechanism of action, it is believed that the presently disclosed therapeutic effect of low molecular weight modified pectins and/or low molecular weight modified -alginates generally is related to their ability to bind various detrimental agents in the circulatory system of the treated individual. The following detailed description of the preferred embodiments is illustrative and is not intended to limit the present invention.

U.S. Pat. Nos. 6,274,566 and 6,462,029, incorporated herein by reference in their entirety, disclose among other things the manufacture and use of compositions comprising low molecular weight modified pectins, including MCP and POS, and low molecular weight modified alginates. These patents particularly disclose the manufacture and use of chemically or enzymatically modified pectins and alginates having an average molecular weight of 40,000 daltons or less.

Algin, pectin, and digestion products of each are known gelling agents. Algins are principally found in seaweed, while pectins are principally found in citrus fruit. Alginates comprise repeating subunits of polyguluronic acid bound by glycosidic linkages at the 1a-4a-di-axial position and repeating subunits of polymannuronic acid bound by galactic links at the 1e-4e di-equatorial position. Pectins are polymers of galacturonic acid, which may be partially esterified. Naturally occurring algins and pectins are high molecular weight products; however, both can be reduced to low molecular weight products either by chemical treatment, e.g., alkaline hydrolysis, or by enzymatic degradation. "Modified pectins" refer to low molecular weight products with an average molecular weight of 40,000 daltons or less obtained by hydrolysis or enzymatic digestion of pectin.

Low molecular weight pectins can be obtained from commercial sources, and methods for obtaining low molecular weight pectins are known in the art. See, e.g., Pienta et al., *J. Nat'l Cancer Inst.*, 87: 348-52 (1995). The final modified pectin is water soluble and has an average molecular weight of 40,000 daltons or less. Preferably, the modified pectin has an average molecular weight between about 10,000 daltons and about 20,000 daltons. More preferably, the modified alginate or modified pectin has an average molecular weight of about 10,000 daltons. The modified pectin also preferably has a degree of esterification of less than about 10%.

Pectins and alginates generally are well tolerated through both oral and intravenous methods of administration. Neither is known to have any side effects or to exhibit cytopathology or toxicology, and when delivered orally, both are of sufficiently low molecular weight and sufficiently water-soluble to be readily absorbed intrabucally or through the intestinal mucosa into the bloodstream. Dosage levels may vary from 5-1,500 mg/kg body weight/day and may be sustained over a prolonged period. A preferred range is 10 mg/kg/day to 1,000 mg/kg/day. For example, modified pectin powder may be encapsulated into gelatin capsules in the amount of 800 mg/capsule. Alternatively, a water-based preparation may be used, e.g., 6 capsules taken three times a day with 8 full ounces of water or juice. Controlled dosage formulations are preferred to ensure adequate medication over time. Compositions comprising modified pectin may be administered over a substantial time period, since the compositions are well tolerated. In one embodiment, the composition is administered over 4-8 weeks or longer, preferably 6 weeks or more. Oral administration is preferred for such long treatment regimens.

Modified pectin and/or modified alginate may be combined with a wide variety of pharmaceutically acceptable carriers, conventional excipients, flavorings and the like that are suitable for oral or intravenous administration, depending on the treatment method desired. The use of such compounds is well known in the art. The modified pectin and/or modified alginate also may be administered with agents that enhance binding, such as glutathione-rich whey protein and related binding adjuvants. Other agents that potentiate the effects of the modified pectin and/or modified alginate composition include methylsulphonylmethane (MSM) and sulfured amino acids, such as N-acetyl cystein, cystein, and methionine, EDTA, inducers of phase II detoxification enzymes, cilantro, garlic, minerals, especially selenium and zinc, anti-oxidants, such as alpha lipoic acid and L-carnitine, curcumin, indoles, and glutathione. Potentiating herbs and other botanicals include detoxifying herbs, such as taraxacum, milkthistle, and Oregon Grape extract, and herbs that increase circulation, such as ginkgo and *Salvia miltiorrhizae*. Additional effective compounds include diuretics or agents that aid excretion through the kidneys or intestines, such as the elimination herbs solidago, *Smilis glabra*, and *Acorus graminus*. Further agents that potentiate the effects of the modified pectin and/or modified alginate composition include chelating agents, such as 2,3-dimercapto-1-propane-sulphonic acid (DMPS) and DL-2,3-dimercapto-succinic acid (DMSA), which are particularly useful when chelating mercury from an individual. Unmodified (i.e., higher molecular weight, naturally occurring) algin and/or pectin also may be added to the modified alginate and/or modified pectin composition to enhance binding of substances in the intestine. In each case above, the agent may be administered as a component of the composition comprising the modified alginate and/or modified pectin, or it may be administered as a separate composition around the same time as administering the modified alginate and/or modified pectin composition.

The following example is intended to be non-limiting and is exemplary of embodiments contemplated but not shown.

1. Material & Methods.

The following examples detail studies using a mouse model.

1.1. Test Article.

MCP was provided by Hangzhou Centrax Trading, Inc. The recommended dosage of MCP is 6 grams per day for adults (i.e., 0.1 g/kg body weight (BW)). Samples were visually inspected to detect the light-yellow color typical of conforming test articles. The test article was stored at ambient temperature.

1.2. Animals.

Healthy female ICR mice were from The Beijing Weitong Lihua Experimental Animal Technology, Inc. (Lot # SCXKI 1-00-0008).

Study 1: 60 animals having weights from 20.0-22.8g were studied in 4 groups (15 animals/group) for the following functions: organ/body weight ratio; delayed-type hypersensitivity (DTH); peritoneal macrophage function; phagocytosis; 50% hemolytic concentration ($HC_{50}$); and antibody production (i.e., B cell counts).

Study 2: 60 animals having weights from 19.0-20.7 g in 4 groups (15 animals/group) for the following function: carbon clearance activity test.

Study 3: 60 animals having weights from 18.1-19.7 g in 4 groups (15 animals/group) for the following functions: lymphocyte transfer induced by ConA and NK cell activity test.

1.3. Administration Method and Dosage Calculation.

Based on 6 grams/day for adult human dose, the dose was set at 1 g/kg BW for mice (i.e., 10-fold of the human dose). Another dose was at 0.1 g/kg (10-fold lower than the first dose), and a third dose was at 3 g/kg (3-fold higher than the first dose).

Animals were fed with normal food. The test article was dissolved in sterile water and orally administered to mice once a day (QD) at 20 mL/kg BW. Animals in the control group were dosed with sterile water only.

1.4. Methods.

1.4.1. Organ-to-body Weight Ratio Determination.

Mice were weighed and then euthanized by cervical dislocation. Their spleens and thymuses were excised and washed, and the organs were weighed. The organ-to-body weight ratio was calculated.

1.4.2. Delayed-type Hypersensitivity (DTH).

Mice were tested for DTH with sheep red blood cell (SRBC) immunization. 2% packed SRBC were suspended in saline, and 0.2 mL of the suspension were administered i.p. to mice for four consecutive days. The thickness of the left-back toes were measured three times, and the average value was calculated. The mice were then injected intradermally with 20 μL of 20% sheep red blood cells suspended in saline in the flipper webbing between two toes on the fifth day. The thickness of the skin was measured using a digital micrometer as a quantitative evaluation of cellular immunity before and 24 hr after the injection. (The difference between the left-front and left-back toes was measured for the evaluation.) MCP was positive in the DTH test if the animals fed with MCP swelled and increased skin thickness significantly.

1.4.3. ConA-mediated Lymphocyte Transformation Assay (MTT Method): Lymphocyte Proliferation Test.

A spleen cell suspension was prepared in Hank's solution, washed three times with Hanks solution, and mixed with 2 mL total culture medium. Cell numbers were counted and adjusted to a concentration of $2\times10^6$ cells/ml. Cells were transferred 1 mL each to two wells in a 24-well culture plate, and 50 μL ConA solution were added to one well, while keeping the other well as a control. The wells were incubated in 5% $CO_2$ at 37° C. for 72 hours. At 68 hour, 0.7 mL of supernatant were taken from each well, and 0.7 mL of RPMI 1640 culture medium without calf serum were added. At the same time, 50 μL MTT (5 mg/mL) were added to each well. Culture was continued for 72 hours. After incubation, 1 mL acidified isopropanol was added to each well, and the solution was mixed until purple crystals disappeared. Absorbance at 570 nm was measured using an enzyme labeling device. Lymphocyte proliferation ability was measured by the absorption value of the ConA sample minus that of the control samples. A Stimulating Index ("SI") was used to evaluate the lymphocyte transformation, where SI=(absorbance in the experiment well)/(absorbance in the control well).

1.4.4. B Cell Counts (Modified Jerne's Method).

Antibody production against sheep red blood cells (SRBC) was determined. Mice were killed after 5 days of i.p. immunization with 0.2 mL of 2% SRBC, and their spleens were removed. Spleen cells were suspended by adding a double volume of Hank's solution and pre-heated agar. 0.5 mL of the suspension were mixed with 50 μL of 10% SRBC in SA buffer and 20 μL spleen cells. The resulting suspension was mixed and spread on slides coated with a thin layer of agar. The slides were incubated in 5% $CO_2$ for 90 min, complement diluted 1:10 with SA buffer was added, and the slides were incubated for another 90 min to form hemolytic plaques. If the number of hemolytic plaques was statistically higher than the control group, then the result was positive.

1.4.5. 50% Hemolytic Concentration ($HC_{50}$).

Semi-quantitative analysis of antibody production against sheep red blood cells (SRBC) was performed as an additional humoral immunologic function of mice treated with 0.2 mL of 2% SRBC by i.p. injection. Blood was drawn through an eye vein after 5 days of immunization with SRBC. Serum was isolated by centrifugation at 2000 rpm for 10 min and then diluted 1:400 with AS buffer. 1 mL of diluted serum was added to 0.5 mL of 10% SRBC and 1 mL of complement diluted 1:10 with SA buffer. A serum-free tube was used as a control. Samples were incubated in a water bath at 37° C. for 30 min, and the reaction was stopped by adding ice water. Absorbance (A) at 540 nm was measured using an ELX-800 enzyme labeling device. $HC_{50}$ was calculated as follows:

$$HC_{50} = \text{Sample A/A at 50\% of SRBC lyses} \times \text{Dilution}.$$

If the $HC_{50}$ value was statistically higher than the control group, then MCP was judged as having a positive effect on $HC_{50}$.

1.4.6. Phagocytic Function of Mononuclear Macrophages (Mouse Carbon Clearance Test).

Mice were randomly divided into a negative control group, a positive control group, and groups receiving different doses of MCP. The groups were fed distilled water, milk and different doses of MCP for successive 30 days. Each mouse was injected with Indian ink diluted 1:3.5 times at 0.05 mL/kg BW into a mouse tail vein 30 minutes after the last feeding. In the second minute ($t_2$) and tenth minute ($t_{10}$) after injection, 2 ml of blood were drawn from the postorbital vein with a suction tube that was moistened with a heparin solution, and the blood was diluted in 2 mL 0.1% sodium carbonate solution. Absorbance (A) of the blood solution was then assayed at 600 nm. The following formula was used to calculate the phagocytic function, $$K = (\log_{10} A_2 - \log_{10} A_{10})/(t_{10} - t_2) = (\log_{10} A_2/A_{10})/8.$$

1.4.7. Mice Peritoneal Macrophage Function: Phagocytosis Assays (Chicken RBC).

Adherent peritoneal macrophages were obtained from mice after flushing the abdominal cavity with ice-cold Hank's solution with 1% BSA. Chicken RBCs were prepared as described. After extensively washing away free antibody, 0.5 mL of 1% chicken RBCs were added to adherent macrophages on slides that were prewarmed for 15 min at 37° C. The sample slide (phagocytosis plate) was washed with NS, and non-phagocytosed RBCs were removed by osmotic lysis. The slide was then fixed with methanol for 1 min, stained with Giemsa solution for 15 min, air dried, and counted under microscope at 40× magnification. Phagocytotic rate was calculated by counting the numbers of phagocytosed RBCs divided by the total number of RBCs counted times 100.

1.4.8. NK (Natural Kill) Cell Activity (LDH Method): Cytotoxicity Assay

Murine lymphoma YAC-1 cells were used as a target in an NK assay. The cells were maintained in a complete medium, consisting of RPMI-1640 without phenol red plus 10% of heat-inactivated (56° C., 30 min) fetal calf serum. Target cells were seeded in 96-well U-bottom culture plates. Effector cells, peritoneal leukocytes, were adjusted to $2 \times 10^7$ cells/mL with RPMI-640 and added at an effector/target ratio of 50/1. The plates were centrifuged at 1500 rpm for 5 min to facilitate cell contacts and then incubated for 4 h at 37° C. After incubation, an enzymatic colorimetric assay was used for cytolysis measurements of target cells based on the determination of lactate dehydrogenase (LDH) using tetrazolium salts. LDH activity was measured in the supernatants (100 μL/well) after addition of the enzyme substrate, and absorbance was measured at 490 nm. Three kinds of control measurements were performed: a target spontaneous release (TS), a target maximum release (M), and an effector spontaneous release (ES). To determine the percentage of lysis of target cells, the following equation was used:

$$\% \text{ lysis} = ((E-ES-TS)/(M-ES-TS)) \times 100.$$

E=mean of absorbance in the presence of effector cells, ES=mean of absorbance of effector cells incubated alone, TS=mean of absorbance in target cells incubated with medium alone, and M=mean of maximum absorbance after incubating target cells with the lysis solution.

1.5. Data Processing.

Data were processed using the Stata software.

1.6. Methods for Evaluating Experimental Results.

Four criteria were used to evaluate the immune supporting function of MCP: cell-mediated immune function, humoral immune function, phagocytic function of mononuclear macrophage, and NK cell activity. If the test article induced a positive immune response in two of the four criteria, then it was judged as having an immune supporting function.

Two experiments were used to test cell-mediated immune function, namely DTH and ConA studies. The test article was judged as having positive cell-mediated function if one or more than one of the dose groups in these two studies were positive. This standard also applied to the humoral immune function and phagocytic function of mononuclear macrophages. NK cell activity also was tested. If one or more dose groups produced positive results, MSP was judged as having a positive function.

2. Results.

2.1. Weight Effect of Centrax MCP

TABLE 1

Effect of Centrax MCP on Mice Weight ($\bar{x} \pm SD$)

| Dose (g/kg BW) | Initial Data | | | End Data | | |
|---|---|---|---|---|---|---|
| | No. of Animals | Initial Weight (g) | P Value | No. of Animals | Initial Weight (g) | P Value |
| Study 1 | | | | | | |
| 0.000 | 15 | 21.1 ± 0.5 | | 15 | 28.3 ± 1.9 | |
| 0.100 | 15 | 21.2 ± 0.6 | 0.756 | 15 | 27.8 ± 1.5 | 0.459 |

TABLE 1-continued

Effect of Centrax MCP on Mice Weight ($\bar{x} \pm SD$)

| 1.000 | 15 | 21.2 ± 0.6 | 0.709 | 15 | 28.3 ± 2.7 | 0.979 |
|---|---|---|---|---|---|---|
| 3.000 | 15 | 21.0 ± 0.6 | 0.779 | 15 | 27.8 ± 1.9 | 0.503 |

| | Initial Data | | | End Data | | |
|---|---|---|---|---|---|---|
| Dose (g/kg BW) | No. of Animals | Initial Weight (g) | Dose (g/kg BW) | No. of Animals | Initial Weight (g) | Dose (g/kg BW) |
| Study 2 | | | | | | |
| 0.000 | 15 | 19.9 ± 0.4 | | 15 | 26.6 ± 2.0 | |
| 0.100 | 15 | 19.7 ± 0.4 | 0.348 | 15 | 26.8 ± 1.8 | 0.759 |
| 1.000 | 15 | 19.9 ± 0.4 | 0.969 | 15 | 26.1 ± 1.7 | 0.424 |
| 3.000 | 15 | 19.9 ± 0.6 | 0.844 | 15 | 26.1 ± 1.8 | 0.430 |
| Study 3 | | | | | | |
| 0.000 | 15 | 18.9 ± 0.4 | | 14 | 27.6 ± 1.8 | |
| 0.100 | 15 | 18.8 ± 0.5 | 0.844 | 15 | 27.1 ± 1.6 | 0.431 |
| 1.000 | 15 | 18.8 ± 0.5 | 0.783 | 15 | 27.2 ± 1.3 | 0.582 |
| 3.000 | 15 | 18.9 ± 0.4 | 0.969 | 14 | 26.9 ± 1.5 | 0.264 |

Results: MCP has no effect on weight.

2.2. Effect of Centrax MCP on Mice Spleen/Body Weight Ratio

TABLE 2

Effect of Centrax MCP on Mice Spleen/Body Weight Ratio ($\bar{x} \pm SD$)

| Dose (g/kg BW) | No. of Animals | Spleen/Body Weight Ratio (mg/g) | P Value |
|---|---|---|---|
| 0.000 | 15 | 6.07 ± 0.75 | |
| 0.100 | 15 | 6.07 ± 0.99 | 0.995 |
| 1.000 | 15 | 5.90 ± 0.77 | 0.543 |
| 3.000 | 15 | 6.16 ± 0.61 | 0.755 |

Results: MCP has no effect on the spleen/body weight ratio.

TABLE 3

Effect of Centrax MCP on Mice Thymus/Body Weight Ratio ($\bar{x} \pm SD$)

| Dose (g/kg BW) | No. of Animals | Thymus/Body Weight Ratio (mg/g) | P Value |
|---|---|---|---|
| 0.000 | 15 | 2.97 ± 0.54 | |
| 0.100 | 15 | 2.80 ± 0.74 | 0.500 |
| 1.000 | 15 | 3.22 ± 0.70 | 0.316 |
| 3.000 | 15 | 3.25 ± 0.73 | 0.258 |

Results: MCP has no effect on the thymus/body weight ratio.

2.3. Effect of Centrax MCP on Cell-Mediated Immunity.

TABLE 4

Effect of Centrax MCP on DTH in Mice ($\bar{x} \pm SD$)

| Dose (g/kg BW) | No. of Animals | Toes Swelling (mm) | P Value |
|---|---|---|---|
| 0.000 | 15 | 0.30 ± 0.22 | |
| 0.100 | 15 | 0.33 ± 0.18 | 0.637 |
| 1.000 | 15 | 0.44 ± 0.20 | 0.070 |
| 3.000 | 15 | 0.52 ± 0.24** | 0.005 |

**$P < 0.01$

Results: MCP had a statistically significant effect on the 3 g/kg group compared to the control group; therefore, MCP stimulates delayed-type hypersensitivity.

TABLE 5

Effect of Centrax MCP on Con A-Mediated Lymphocyte Transformation in Mice ($\bar{x} \pm SD$)

| Dose (g/kg BW) | No. of Animals | Lymphocyte Proliferation (OD Difference) | Statistical Data Processing | P Value |
|---|---|---|---|---|
| 0.000 | 14 | 0.265 ± 0.063 | 23.3 ± 13.7 | |
| 0.100 | 15 | 0.354 ± 0.110 | 38.4 ± 17.0* | 0.015 |
| 1.000 | 15 | 0.338 ± 0.178 | 31.2 ± 17.9 | 0.191 |
| 3.000 | 14 | 0.274 ± 0.084 | 24.3 ± 15.5 | 0.871 |

*$P < 0.05$

Results: MCP had a statistically significant on the 0.1 g/kg group compared to the control group; therefore, MCP enhances ConA-mediated lymphocyte transformation. Accordingly, MCP positively affected two cell-mediated immune functions (see Tables 4 and 5); therefore, MCP boosts cell-mediated immunity.

2.4. Effect of Centrax MCP on Humoral Immunity.

TABLE 6

Effect of Centrax MCP on Antibody Production Cells Counts ($\bar{x} \pm SD$)

| Dose (g/kg BW) | No. of Animals | No. of Hemolytic Plaque (×10³/Whole Spleen) | P Value |
|---|---|---|---|
| 0.000 | 15 | 101 ± 51 | |
| 0.100 | 13 | 79 ± 95** | 0.005 |
| 1.000 | 15 | 165 ± 61* | 0.014 |
| 3.000 | 15 | 158 ± 68* | 0.030 |

*$P < 0.05$
**$P < 0.01$

Results: All groups generated statistically significant positive results.

TABLE 7

Effect of Centrax MCP to $HC_{50}$ Value ($\bar{x} \pm SD$)

| Dose (g/kg BW) | No. of Animals | $HC_{50}$ Value | P Value |
|---|---|---|---|
| 0.000 | 15 | 280 ± 56 | |
| 0.100 | 13 | 321 ± 58 | 0.136 |
| 1.000 | 15 | 259 ± 99 | 0.418 |
| 3.000 | 15 | 268 ± 60 | 0.622 |

Results: No statistically significant results were obtained.

One study showed a positive outcome for all 3 dosing groups; the other study did not show statistically significant positive result. MCP thus boosts humoral immune function, following the disclosed method of evaluating experimental results.

2.5. Effect of Centrax MCP on the Phagocytic Function of Mononuclear Macrophage in Mice.

TABLE 8

Effect of Centrax MCP on Mononuclear Macrophage Carbon Clearance ($\bar{x} \pm SD$)

| Dose (g/kg BW) | No. of Animals | Phagocytic Index (a) | P Value |
|---|---|---|---|
| 0.000 | 15 | 5.09 ± 0.97 | |
| 0.100 | 14 | 5.79 ± 0.73* | 0.030 |
| 1.000 | 15 | 5.01 ± 0.87 | 0.810 |
| 3.000 | 15 | 5.04 ± 0.78 | 0.866 |

*$P < 0.05$

Results: MCP had a statistically significant positive effect on the 0.1 g/kg group compared to the control group.

TABLE 9

Effect of Centrax MCP on Macrophage Phagocytosis of Chicken Red Cells ($\bar{x} \pm SD$)

| Dose (g/kg BW) | No. of Animals | Phagocytosis (%) | Statistical Data Processing | P Value |
|---|---|---|---|---|
| 0.000 | 15 | 35 ± 12 | 36 ± 7 | |
| 0.100 | 15 | 35 ± 11 | 36 ± 7 | 0.946 |
| 1.000 | 15 | 46 ± 13 | 42 ± 8* | 0.015 |
| 3.000 | 15 | 52 ± 9 | 46 ± 5** | 0.000 |

*$P < 0.05$
**$P < 0.01$

Results: MCP had a statistically significant positive effect on the 1 g/kg and 3 g/kg groups compared to the control group.

TABLE 10

Effect of Centrax MCP on the Phagocytic Index of Mouse Macrophage in the Phagocytosis of Chicken Red Blood Cells ($\bar{x} \pm SD$)

| Dose (g/kg BW) | No. of Animals | Phagocytic Index | P Value |
|---|---|---|---|
| 0.000 | 15 | 0.49 ± 0.18 | |
| 0.100 | 15 | 0.47 ± 0.17 | 0.670 |
| 1.000 | 15 | 0.63 ± 0.17* | 0.029 |
| 3.000 | 15 | 0.69 ± 0.17** | 0.003 |

*$P < 0.05$
**$P < 0.01$

Results: MCP produced positive results in the two dosing groups. Accordingly, results from the two studies (carbon clearance and chicken RBC phagocytosis) showed positive results in multiple dosing groups (see Tables 8, 9 and 10); therefore, MCP had positive function in mononuclear macrophage phagocytosis.

2.6. The Effect of Centrax MCP on Mouse NK Cell Activity.

TABLE 11

The Effect of Centrax MCP on Mouse NK Cell Activity ($\bar{x} \pm SD$)

| Dose (g/kg BW) | No. of Animals | NK Cell Activity (%) | NK Cell Activity Statistical Data Processing | P Value |
|---|---|---|---|---|
| 0.000 | 14 | 54.9 ± 11.3 | 47.9 ± 6.7 | |
| 0.100 | 15 | 67.7 ± 8.1 | 55.6 ± 5.3** | 0.000 |
| 1.000 | 15 | 68.5 ± 7.6 | 56.0 ± 4.6** | 0.000 |
| 3.000 | 14 | 65.1 ± 8.4 | 54.0 ± 5.3** | 0.006 |

**$P < 0.01$

Results: All three dosing groups showed strong positive results; therefore, MCP has a positive immune supporting function, based on the NK cell activity criterion.

3. Conclusions.

After oral administration of MCP to mice for 30 days, the animals showed positive responses in cell-mediated immune function, humoral immune function, phagocytic function of mononuclear macrophages, and NK cell activity. No effect of the test article on animal weight, thymus/body weight ratio, spleen/body weight ratio was observed. Accordingly, it was concluded that Centrax MCP has an immune boosting function.

Numerous modifications and variations of the present invention are possible in light of the above teachings; therefore, one of skill in the art reading this disclosure could change various details without departing from the true scope of the invention.

What is claimed is:

1. A method of stimulating an immune response in a mammal, comprising selecting a mammal exhibiting an inadequate or reduced immune function characterized by at least one of a cell-mediated immunity below average in said mammal, a humoral immunity below average in said mammal, phagocyte mononuclear macrophage function below average in said mammal or NK cell activity below average in said mammal, and administering to said mammal a composition comprising an agent effective to stimulate an immune response in said mammal, wherein said agent consists of a modified pectin, a modified alginate, or a combination of a modified pectin and a modified alginate, where the modified alginate or modified pectin has an average molecular weight of 40,000 daltons or less, where the modified alginate or modified pectin is present in an amount effective to stimulate an immune response in said mammal.

2. The method of claim 1, where the stimulation of the immune response modulates, supports, enhances or extends the immune response in the mammal.

3. The method of claim 1, where the stimulation of the immune response comprises stimulation of cell-mediated immune function.

4. The method of claim 1, where the stimulation of the immune response comprises stimulation of humoral immune function.

5. The method of claim 1, where the stimulation of the immune response comprises stimulation of phagocytic function of mononuclear macrophages.

6. The method of claim 1, where the stimulation of the immune response comprises stimulation of NK cell activity.

7. The method of claim 1, where the mammal's immune function is compromised by disease or administration of a drug.

8. The method of claim 1, where the modified pectin is modified citrus pectin (MCP).

9. The method of claim 1, where the modified pectin is pectin oligosaccharide (POS).

10. The method of claim 1, where the mammal is a human.

11. The method of claim 1, where the composition is administered orally.

12. The method of claim 1, where the composition is administered intravenously.

13. The method of claim 1, where the modified alginate or modified pectin has an average molecular weight between about 10,000 daltons and about 20,000 daltons.

14. The method of claim 13, where the modified alginate or modified pectin has an average molecular weight of about 10,000 daltons.

15. The method of claim 1, where the modified alginate or modified pectin has a degree of esterification of less than about 10%.

16. The method of claim 1, where the modified alginate or modified pectin is administered at an amount of 5-1,500 mg/kg body weight/day.

17. The method of claim 16, where the modified alginate or modified pectin is administered at an amount of 10-1,000 mg/kg body weight/day.

18. The method of claim 1, where the composition is administered to the mammal for more than four weeks.

19. The method of claim 18, where the composition is administered for more than six weeks.

20. The method of claim 1, further comprising administering an agent that potentiates the effect of modified alginate or modified pectin.

21. The method of claim 20, where the agent is methylsulphonylmethane (MSM), a sulfured amino acid, EDTA, an inducer of phase II detoxification enzymes, cilantro, garlic, a mineral, an anti-oxidant, curcumin, an indole, or glutathione.

22. The method of claim 20, where the agent is a potentiating herb or botanical.

23. The method of claim 22, where the herb or botanical is taraxacum, milkthistle, Oregon Grape extract, ginkgo, or *Salvia Miltiorrhizae*.

24. The method of claim 20, where the agent is a diuretic or aids excretion through the kidneys or intestines.

25. The method of claim 24, where the agent is solidago, *Smilis Glabra*, or *Acorns Graminus*.

26. The method of claim 20, where the agent chelates mercury.

27. The method of claim 26, where the agent is 2,3-dimercapto-1-propane-sulphonic acid (DMPS) or DL-2,3-dimercapto-succinic acid (DMSA).

28. The method of claim 1, further comprising administering unmodified algin or pectin.

* * * * *